United States Patent
Wakizaka et al.

(10) Patent No.: US 10,766,040 B2
(45) Date of Patent: Sep. 8, 2020

(54) ANALYSIS DEVICE AND SEPARATION DEVICE

(71) Applicants: AFI Corporation, Kyoto (JP); Kyoto University, Kyoto (JP)

(72) Inventors: Yoshikazu Wakizaka, Hyogo (JP); Masayo Takano, Tokyo (JP); Takayuki Itoi, Osaka (JP); Takaharu Enjoji, Tokyo (JP); Masakazu Toi, Kyoto (JP); Tomomi Nishimura, Kyoto (JP)

(73) Assignee: AFI CORPORATION, Kyoto (JP)

( * ) Notice: Subject to any disclaimer, the term of this patent is extended or adjusted under 35 U.S.C. 154(b) by 92 days.

(21) Appl. No.: 16/073,770

(22) PCT Filed: Jan. 27, 2017

(86) PCT No.: PCT/JP2017/002943
§ 371 (c)(1),
(2) Date: Jul. 27, 2018

(87) PCT Pub. No.: WO2017/131162
PCT Pub. Date: Aug. 3, 2017

(65) Prior Publication Data
US 2019/0032103 A1    Jan. 31, 2019

(30) Foreign Application Priority Data
Jan. 29, 2016    (JP) .................. 2016-016119

(51) Int. Cl.
*C12M 1/34* (2006.01)
*B03C 5/02* (2006.01)
(Continued)

(52) U.S. Cl.
CPC ........ *B03C 5/022* (2013.01); *B01L 3/502761* (2013.01); *C12M 1/34* (2013.01);
(Continued)

(58) Field of Classification Search
CPC ................ B03C 5/022; G01N 15/1031; G01N 2015/1081; G01N 2015/1006;
(Continued)

(56) References Cited

U.S. PATENT DOCUMENTS

| 6,790,330 B2 | 9/2004 | Gascoyne et al. |
| 2002/0036142 A1 | 3/2002 | Gascoyne et al. |

(Continued)

FOREIGN PATENT DOCUMENTS

| CN | 102465094 A | 5/2012 |
| CN | 104651315 A | 5/2015 |

(Continued)

OTHER PUBLICATIONS

International Patent Application No. PCT/JP2017/002943; Int'l Preliminary Report on Patentability; dated Aug. 9, 2018; 6 pages.

(Continued)

*Primary Examiner* — J. Christopher Ball
(74) *Attorney, Agent, or Firm* — BakerHostetler (57) ABSTRACT

An analysis device (200) analyzes a crossover frequency at which a dielectrophoretic force on dielectric particles switches from a repulsive force to an attractive force or from the attractive force to the repulsive force, comprising a flow channel (5), a pair of electrodes (22, 23), a power supply (24), an imaging unit (25) and an analyzer (26). Through the flow channel (5), a sample solution containing the dielectric particles in the dielectrophoretic liquid flows. The pair of electrodes (22, 23) are arranged in the first channel. The power supply (24) applies a frequency-modulated AC voltage to the first electrodes (22, 23). The imaging unit (25) captures an image of a movement trajectory of each of the dielectric particles flowing between the electrodes (22, 23) in the flow channel. The analyzer (26) obtains the crossover frequency of the dielectric particles based on the captured image of the movement trajectory.

4 Claims, 4 Drawing Sheets

(51) Int. Cl.
  *B01L 3/00* (2006.01)
  *C12Q 1/04* (2006.01)
  *G01N 15/10* (2006.01)
(52) U.S. Cl.
  CPC .......... *C12Q 1/04* (2013.01); *G01N 15/1031* (2013.01); *B01L 2200/0652* (2013.01); *B01L 2300/0645* (2013.01); *B01L 2400/0424* (2013.01); *G01N 2015/1006* (2013.01); *G01N 2015/1081* (2013.01)
(58) Field of Classification Search
  CPC ....... B01L 3/502761; B01L 2400/0424; B01L 2200/0652
  See application file for complete search history.

(56) References Cited

U.S. PATENT DOCUMENTS

| | | |
|---|---|---|
| 2004/0060820 A1 | 4/2004 | Bressler |
| 2007/0091450 A1 | 4/2007 | Detro et al. |
| 2010/0219075 A1 | 9/2010 | Furusawa |
| 2012/0273357 A1 | 11/2012 | Katsumoto et al. |
| 2013/0292247 A1* | 11/2013 | Peyrade ................. B03C 5/005 204/518 |
| 2017/0028408 A1 | 2/2017 | Menachery et al. |

FOREIGN PATENT DOCUMENTS

| | | |
|---|---|---|
| EP | 2042239 A1 | 4/2009 |
| JP | 2013-127418 A | 6/2013 |
| WO | WO 2001/096025 A2 | 12/2001 |
| WO | WO 2007/091450 A1 | 8/2007 |
| WO | WO 2007/019450 A1 | 7/2009 |
| WO | WO 2015/157072 A1 | 10/2015 |

OTHER PUBLICATIONS

Pethig et al.; "Cell Physiometry Tools Based on Dielectrophoresis"; Journal of the Association for Laboratory Automation; vol. 9; Oct. 2004; p. 324-330.

European Patent Application No. 17744392.6; Extended Search Report; dated Jul. 29, 2019; 8 pages.

Yafouz et al.; "Dielectrophoretic Manipulation and Separation of Microparticles Using Microarray Dot Electrodes"; Sensors; vol. 14(4); 2014; p. 6536-6369.

International Patent Application No. PCT/JP2017/002943; Int'l Written Opinion and the Search Report; dated Apr. 25, 2017; 5 pages.

China Patent Application No. 201780008886.6; Office Action; dated Mar. 16, 2020; 15 pages.

* cited by examiner

ANALYSIS DEVICE AND SEPARATION DEVICE

CROSS-REFERENCE TO RELATED APPLICATION

This application is a U.S. national application of International Application No. PCT/JP2017/002943, filed Jan. 27, 2017, which claims priority to and benefits of Japanese Patent Application No. 2016-016119, filed on Jan. 29, 2016, the disclosures of which are incorporated herein by reference in their entireties.

TECHNICAL FIELD

The present invention relates to an analysis device for analyzing a crossover frequency at which a dielectrophoretic force on dielectric particles, such as bacteria and cells, switches from a repulsive force to an attractive force or from the attractive force to the repulsive force, and relates to a separation device for separating the dielectric particles.

BACKGROUND ART

There is known a separation technique for separating dielectric particles such as bacteria and cells by using dielectrophoresis, and in order to separate this type of dielectric particles, there is known an analysis technique for analyzing a crossover frequency at which a dielectrophoretic force on the dielectric particles switches from a repulsive force to an attractive force or from the attractive force to the repulsive force.

Patent Document 1 discloses a characteristic analysis method of optimizing an AC voltage frequency to be applied in performing characteristic analysis on particulate matter by using dielectrophoresis. This characteristic analysis method includes the steps of: selecting at least one particulate matter in a fluid; positioning the selected particulate matter in the vicinity of a pair of electrodes; generating a spatially inhomogeneous electric field between the pair of electrodes by using a programmed voltage signal including a frequency-modulated AC voltage; detecting the movement of the particulate matter while applying the programmed voltage signal to create time-series data on the movement of the particulate matter; and analyzing the characteristics of the particulate matter based on the time-series data. The time series data is moving image data obtained by capturing an image of movement of the particulate matter, and the moving image data includes data of imaging time. The step of analyzing the characteristics of the particulate matter includes the steps of: displaying data of the imaging time together with the moving image data on a display; obtaining the time when the selected particulate matter stays in the vicinity of the tip of one of the pair of electrodes based on the moving image data displayed on the display, and calculating a boundary frequency at which the dielectrophoretic force on the selected particulate matter switches from the attractive force to the repulsive force based on the obtained time.

CITATION LIST

Patent Document

Patent Document 1: International Publication No. 2007/091450

SUMMARY OF INVENTION

Technical Problems

In the characteristic analysis method disclosed in Patent Document 1, the operation of positioning dielectric particles (particulate matter) between fine microelectrodes is complicated. In addition, the characteristic analysis method disclosed in Patent Document 1 is specialized for measuring the crossover frequency, and the measured dielectric particles cannot be separated as they are.

An object of the present invention is to provide an analysis device and a separation device capable of easily analyzing a crossover frequency of dielectric particles and allowing the dielectric particles to be used after the analysis.

Solutions to Problems

An analysis device according to the present invention is an analysis device for analyzing a crossover frequency at which a dielectrophoretic force on dielectric particles switches from a repulsive force to an attractive force or from the attractive force to the repulsive force, the analysis device including a first flow channel, a pair of first electrodes, a first power supply, an imaging unit, and an analyzer. A sample solution containing the dielectric particles in the dielectrophoretic liquid flows through the first flow channel. The pair of first electrodes is arranged in the first flow channel, and the first power supply applies a frequency-modulated AC voltage to the pair of first electrodes. The imaging unit captures an image of a movement trajectory of each of the dielectric particles flowing between the pair of first electrodes in the first flow channel. The analyzer obtains the crossover frequency of the dielectric particles based on the captured image of the movement trajectory.

A separation device according to the present invention is a separation device for separating dielectric particles, the separation device including the above analysis device, a pair of second electrodes, and a controller. The pair of second electrodes is arranged at a stage subsequent to the pair of first electrodes in the first flow channel of the analysis device, and the second power supply applies an AC voltage of a predetermined frequency to the pair of second electrodes. The controller controls the predetermined frequency based on the crossover frequency obtained by the analysis device with respect to the dielectric particles so that the dielectric particles analyzed by the analysis device are subjected to dielectrophoresis at the time of passage of the dielectric particles through the pair of second electrodes in the first flow channel.

Advantageous Effects of Invention

According to the present invention, it is possible to easily analyze the crossover frequency of the dielectric particles and to use the dielectric particles after the analysis.

EMBODIMENT OF THE INVENTION

Hereinafter, an embodiment of an analysis device and a separation device according to the present invention will be described with reference to the attached drawings, the analysis device for analyzing a crossover frequency of a dielectrophoretic force on dielectric particles, the separation device for separating the dielectric particles based on the analyzed crossover frequency.

0. Outline of Dielectrophoresis

Before description of the present embodiment, an outline of dielectrophoresis will be described. When electrodes are disposed for a sample solution containing dielectric particles such as bacteria and cells and an AC voltage with a frequency ω is supplied to the electrodes, a dielectrophoretic force acts on the dielectric particles in the sample solution. This dielectrophoretic force $F_{DEP}$ is expressed by the following equation:

$$F_{DEP}=2\pi r^3 \varepsilon_m Re[K(\omega)]\nabla E^2 \quad (1)$$

In Equation (1) above, r is a radius of the dielectric particle, $\varepsilon_m$ is a permittivity of a medium (solution) of the sample solution, and E is an intensity of an electric field. Re[X] represents a real part of a complex number X. $K(\omega)$ is a Clausius-Mossotti factor and is expressed by the following equation:

$$K(\omega)=(\varepsilon_p^* - \varepsilon_m^*)/(\varepsilon_p^* + 2\varepsilon_m^*) \quad (2)$$

In Equation (2) above, $\varepsilon_p^*(=\varepsilon_p + \rho_p/(j\omega))$ is a complex permittivity of the particle ($\varepsilon_p$ is a permittivity (real part) of the particle, $\rho_p$ is a conductivity of the particle). Further, $\varepsilon_m^*(=\varepsilon_m + \rho_m/(j\omega))$ is a complex permittivity of a surrounding medium ($\varepsilon_m$ is a permittivity (real part) of the surrounding medium, $\rho_m$ is a conductivity of the surrounding medium).

Figure 1:
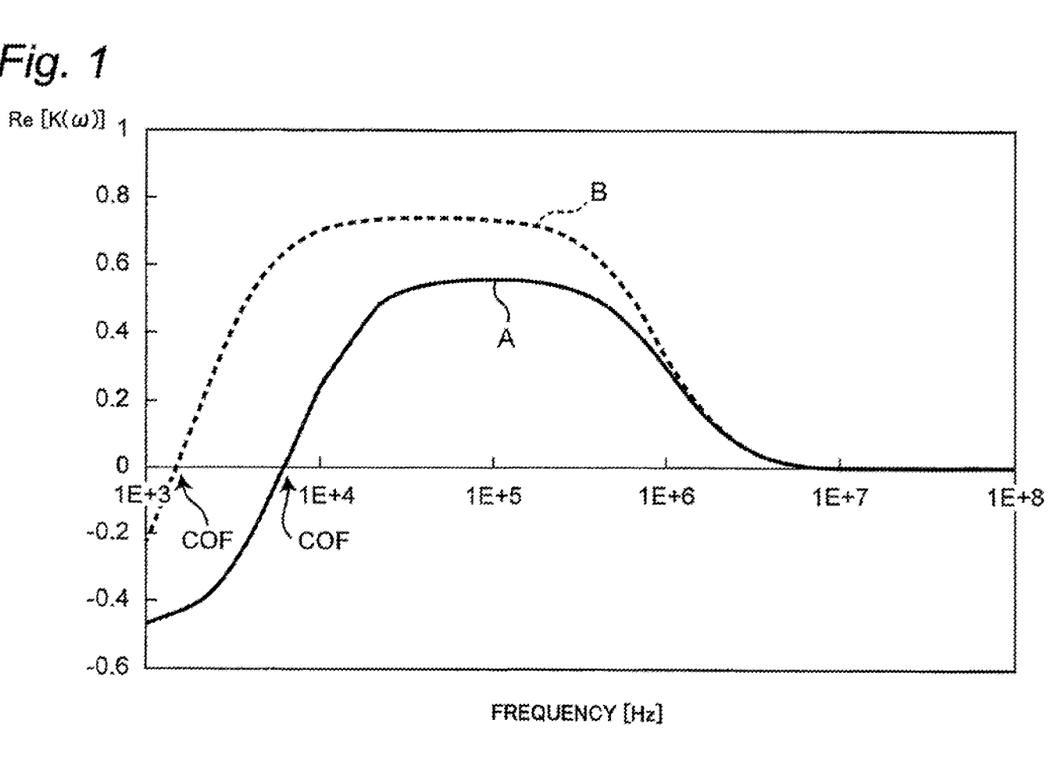
FIG. 1 is a graph showing an example of a frequency characteristic of a Clausius-Mossotti factor with respect to a dielectrophoretic force.

FIG. 1 is a graph showing frequency characteristics of $Re[K(\omega)]$. FIG. 1 shows $Re[K(\omega)]$ of two different dielectric particles A and B. As shown in FIG. 1, $Re[K(\omega)]$ has frequency dependence. When $Re[K(\omega)]>0$, according to Equation (1) above, a positive dielectrophoretic force $F_{DEP}$ (attractive force) acts on the particles with respect to a direction in which the electrode is installed, and the particles are attracted to the vicinity of the electrode. On the other hand, when $Re[K(\omega)]<0$, a negative dielectrophoretic force $F_{DEP}$ (repulsive force) acts on the particles and the electrode repels the particles. A frequency at a boundary where the dielectrophoretic force $F_{DEP}$ changes from positive to negative or vice versa, that is, a frequency at the time when $Re[K(\omega)]=0$ is called a crossover frequency (COF).

As shown in FIG. 1, the frequency characteristic of $Re[K(\omega)]$ differs for the dielectric particles A, B, and the crossover frequency COF also differs for the dielectric particles A, B.

First Embodiment

1. Configuration

In the following description, an apparatus for separating cancer cells contained in blood will be described.

1-1. Separation Device

Figure 2:
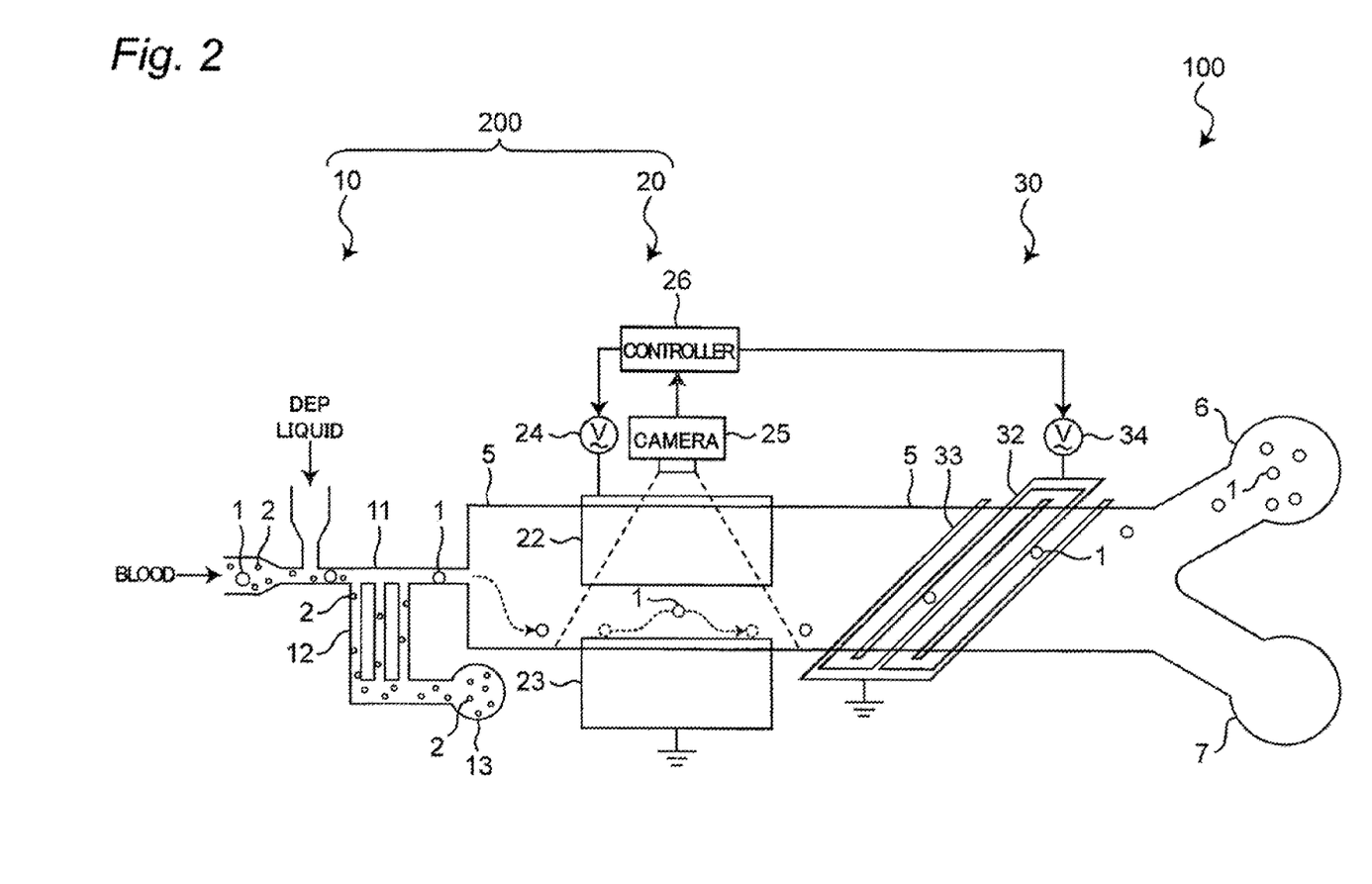
FIG. 2 is a diagram showing a configuration of a separation device and an analysis device according to a first embodiment.

Hereinafter, the separation device of the first embodiment will be described. FIG. 2 is a diagram showing the configuration of the separation device 100 according to the first embodiment. A separation device 100 shown in FIG. 2 includes a flow channel (first flow channel) 5 through which a sample solution containing circulating cancer cells (CTC) 1 flows in a predetermined direction (liquid flowing direction), a replacement unit 10, an analyzer 20, and a separator 30. The replacement unit 10 and the analyzer 20 constitute the analysis device 200.

(1) Replacement Unit

The replacement unit 10 replaces small cells 2 such as red blood cells and a solution in blood (suspension) with a dielectrophoretic liquid (DEP liquid), and only extracts cells of a desired sire or larger, such as the cancer cells 1 and white blood cells contained in the blood. The replacement unit 10 includes a main flow channel (second flow channel) 11, a plurality of branched flow channels 12, and a waste liquid chamber 13. The replacement unit 10 can introduce into the flow channel 5 only the cells of the desired size or larger by changing the flow channel width, the flow channel height, and the flow channel length of each of the main flow channel 11 and the branched flow channels 12.

The main flow channel 11 is disposed at a stage prior to the flow channel 5 and forms a flow channel continuing to the flow channel 5. The blood containing the cancer cells 1 and the DEP liquid are introduced into the main flow channel 11. The blood is introduced in the liquid flowing direction of the main flow channel 11, and the DEP liquid is introduced in a direction orthogonal to the liquid flowing direction of the main flow channel 11. The width of the main flow channel 11 may only be substantially equal to or larger than the diameters of cells such as the cancer cells 1 and the white blood cells. The width of the main flow channel 11 may be about 10 μm or larger and about 100 μm or smaller, more preferably 20 μm or larger and 60 μm or smaller.

The branched flow channels 12 are disposed at substantially equal intervals in the liquid flowing direction at a stage subsequent to the introduction portion for the DEP liquid in the main flow channel 11. The branched flow channels 12 are arranged on the side opposite to the inflow portion of the DEP liquid in the main flow channel 11. The width of each branched flow channel 12 is smaller than the width of the main flow channel 11.

According to this configuration, the cells 2 such as the red blood cells and the solution in the blood are diverted into the branched flow channels 12, and the cells of the desired size or larger, such as the cancer cells 1 and the white blood cells, and the DEP liquid flow in the main flow channel 11. Hence in the main flow channel 11, the cells 2 such as the red blood cells and the solution in the blood are replaced with the DEP liquid, and a sample solution is produced containing the cells of the desired size or larger, such as the cancer cells 1 and the white blood cells in the DEP liquid. The main flow channel 11 individually and sequentially leads the cells such as the cancer cells 1 and the white blood cells in the sample solution from the main flow channel 11 to the flow channel 5 described above.

The waste liquid chancer 13 is a chamber that stores the cells 2 such as the red blood cells and the solution diverted into the branched flow channels 12.

(2) Analyzer

The analyzer 20 analyzes a crossover frequency of a dielectrophoretic force on the cells such as the cancer cells 1 and the white blood cells in the sample solution flowing through the flow channel 5. The analyzer 20 includes a pair of electrodes (first electrodes) 22, 23, a power supply (first power supply) 24, an imaging unit 25, and a controller (analyzer) 26.

In the flow channel 5, the electrodes 22, 23 are arranged to face each other in a direction orthogonal to the liquid flowing direction of the flow channel 5. The electrode 23 is grounded, and the electrode 21 is supplied with an AC voltage from the power supply 24.

Figure 3:
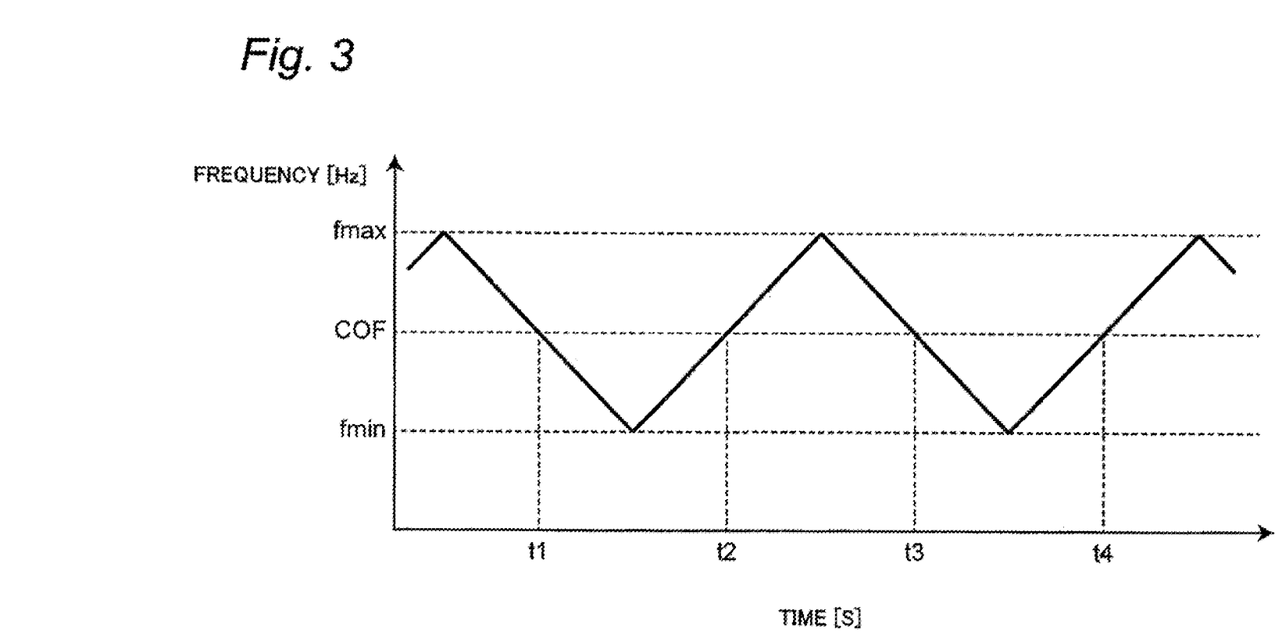
FIG. 3 is a graph showing an example of a change in frequency of an AC voltage in the analysis device.

The power supply 24 is a function generator, for example. Under the control of the controller 26, the power supply 24 generates a frequency-modulated AC voltage and supplies the generated AC voltage between the electrodes 22, 23. FIG. 3 is a graph showing an example of a change in the frequency of the AC voltage. As shown in FIG. 3, the power supply 24 generates an AC voltage with a frequency periodically changed in the frequency range from fmin to fmax.

According to such a configuration, the dielectrophoretic force acting on the cells such as the cancer cells 1 and the white blood cells passing between the pair of the electrodes 22, 23 changes periodically.

The imaging unit 25 includes a camera having an imaging element such as a CCD image sensor or a CMOS image sensor, and an optical microscope module. The optical microscope module may be a phase contrast microscope or an epi-illumination microscope. Further, the optical microscope module may be configured to be switchable between the phase contrast microscope and the epi-illumination microscope by, for example, exchanging lenses. When fluorescence observation is to be performed, a fluorescence filter is used as appropriate. The imaging unit 25 captures images of the cells such as the cancer cells 1 and the white blood cells passing between the pair of the electrodes 22, 23 and outputs the captured images to the controller 26. The imaging operation of the imaging unit 25 may be controlled by the controller 26.

The controller 26 is a personal computer, for example. The controller 26 includes a storage such as an HDD and an SSD, and a controller such as a CPU, and the controller executes a program stored in the storage to achieve various functions. For example, the controller 26 performs image analysis on the image captured by the imaging unit 25 and determines the movement trajectory of each of the cells such as the cancer cells 1 and the white blood cells passing between the pair of the electrodes 22, 23. Note that the controller 26 may store the captured image of the imaging unit 25 in the storage and perform image analysis on the stored captured image. Further, the controller 26 may include a liquid crystal display or an organic EL display and may display the captured image of the imaging unit 25 or the movement trajectory obtained by image analysis.

(3) Separator

The separator 30 is provided at the stage subsequent to the analyzer 20 in the flow channel 5 and separates the cancer cells 1 based on the crossover frequency of the cells such as the cancer cells 1 and the white blood cells analyzed by the analyzer 20. The separator 30 includes a pair of electrodes (second electrodes) 32, 33, a power supply (second power supply) 34, and collection units 6, 7.

The electrodes 32, 33 each have a comb shape arranged at regular intervals. A plurality of protrusions in the comb shape of the two electrodes 32, 33 are alternately arranged at predetermined intervals in the liquid flowing direction of the flow channel 5. Each of the protrusions of the electrodes 32, 33 extends in a direction obliquely intersecting with the liquid flowing direction so as to form an acute angle of, for example, 10° to 60° both inclusive, with respect to the liquid flowing direction.

The power supply 34 is a function generator, for example. When the cancer cell 1 passes through the electrodes 32, 33 under the control of the controller 26 in the analyzer 20, the power supply 34 generates an AC voltage having a frequency that is higher than the crossover frequency obtained by the analyzer 20 with respect to the cancer cells 1 and is in the vicinity of the crossover frequency obtained by the analyzer 20 with respect to the cells other than the cancer cells 1, such as the white blood cells, and supplies the generated AC voltage between the electrodes 32, 33.

Thus, a positive dielectrophoretic force (attractive force) acts on the cancer cells 1, and the cancer cells 1 flow in the flow channel 5 along the extending direction of the electrodes 32, 33, while being attracted to the electrodes 32, 33, to be collected to the collection unit 6. On the other hand, no dielectrophoretic force acts on the cells such as the white blood cells, or even if a positive or negative dielectrophoretic force (attractive force or repulsive force) acts thereon, the dielectrophoretic force is relatively small. Therefore, the cells such as the white blood cells are allowed to flow by the flow in the flow channel 5 and are collected into the collection unit 7.

The collection unit 6 is for separating and collecting the cancer cells 1 having flown through the flow channel 5, and the collection unit 7 is for collecting unnecessary white blood cells and the like.

2. Operation

Hereinafter, the operation of the separation device 100 will be described. As shown in FIG. 2, in the separation device 100, the replacement unit 10 replaces the cells 2 such as the red blood cells and the solution in the blood with the DEP liquid, and only extracts the cells of the desired size or larger, such as the cancer cells 1 and the white blood cells contained in the blood. The analyzer 20 analyses the crossover frequency of the dielectrophoretic force on the extracted cells such as the cancer cells 1 and the white blood cells. The separator 30 separates the cancer cells 1 based on the crossover frequency of the cells such as the cancer cells 1 and the white blood cells analyzed by the analyzer 20. Hereinafter, the operation of the separation device 100 will be described in detail.

First, the blood containing the cells such as the cancer cells 1 and the white blood cells is introduced into the main flow channel 11 of the replacement unit 10 in the liquid flowing direction of the main flow channel 11, and at the same time, the DEP liquid is introduced in the direction orthogonal to the liquid flowing direction of the main flow channel 11. The cells 2 such as the red blood cells and the solution in the blood are diverted into the branched flow channels 12, and the cells of the desired size or larger, such as the cancer cells 1 and the white blood cells, and the DEP liquid flow in the main flow channel 11. In this manner, the replacement unit 10 performs solution replacement (buffer replacement), generates a sample solution containing the cells of the desired size or larger such as the cancer cells 1 and the white blood cells in the DEP liquid and supplies the generated sample solution from the main flow channel 11 to the flow channel 5. At this time, the replacement unit 10 leads the cells such as the cancer cells 1 and the white blood cells one by one from the main flow channel 11 to the flow channel 5.

Under the control of the controller 26, as shown in FIG. 3, the power supply 24 of the analyzer 20 generates an AC voltage with a frequency periodically changed in the frequency range from fmin to fmax, and supplies the generated AC voltage between the electrodes 22, 23. As a result, an AC voltage periodically frequency-modulated is applied between the electrodes 22, 23 in the flow channel 5. As a result, when the cells such as the cancer cells 1 and the white blood cells flowing in the flow channel 5 pass between the electrodes 22, 23, the cells such as the cancer cells 1 and the white blood cells receive a dielectrophoretic force.

At this time, the imaging unit 25 captures images of the cells such as the cancer cells 1 and the white blood cells passing between the pair of the electrodes 22, 23. The controller 26 performs image analysis on the image captured by the imaging unit 25 and determines the movement trajectory of the cells such as the cancer cells 1 and the white blood cells passing between the electrodes 22, 23. Based on the obtained movement trajectory, the controller 26 analyzes the timing at which the dielectrophoretic force switches from the repulsive force to the attractive force, obtains the frequency of the AC voltage of the power supply 24 at the timing from control information to the power supply 24 at the timing, and takes the obtained frequency as a crossover frequency (COF). Details of this analysis processing will be described later.

Thereafter, the cells such as the cancer cells 1 and the white blood cells, analyzed by the analyzer 20, flow toward the separator 30. When the analyzed cells such as the cancer cells 1 and the white blood cells pass through the electrodes 32, 33 of the separator 30, the controller 26 controls the power supply 34 so as to generate an AC voltage having a frequency that is higher than the crossover frequency obtained by the analysis with respect to the cancer cells 1 and is in the vicinity of the crossover frequency obtained by the analysis with respect to the cells other than the cancer cells 1, such as the white blood cells. The timing at which the analyzed cells such as the cancer cells 1 and the white blood cells pass through the electrodes 32, 33 of the separator 30 is determined, for example, based on the distance between the electrodes 22, 23 and the electrodes 32, 33, and the flow rate of the sample solution flowing in the flow channel 5. The power supply 34 generates an AC voltage having a frequency based on the control of the controller 26 and supplies the generated AC voltage to the electrode 32. As a result, in the flow channel 5, an AC voltage having the frequency is applied between the electrodes 32, 33. At this time, a positive dielectrophoretic force (attractive force) acts on the cancer cells 1, and the cancer cells 1 flow in the flow channel 5 along the extending direction of the electrodes 32, 33, while being attracted to the electrodes 32, 33, to be collected to the collection unit 6. On the other hand, no dielectrophoretic force acts on the unnecessary cells such as the white blood cells, or even if a positive or negative dielectrophoretic force (attractive force or repulsive force) acts thereon, the dielectrophoretic force is relatively small. Therefore, the cells such as the white blood cells are allowed to flow by the flow in the flow channel 5 and are collected into the collection unit 1.

2-1. Crossover Frequency Analyzing Process

Figure 4:
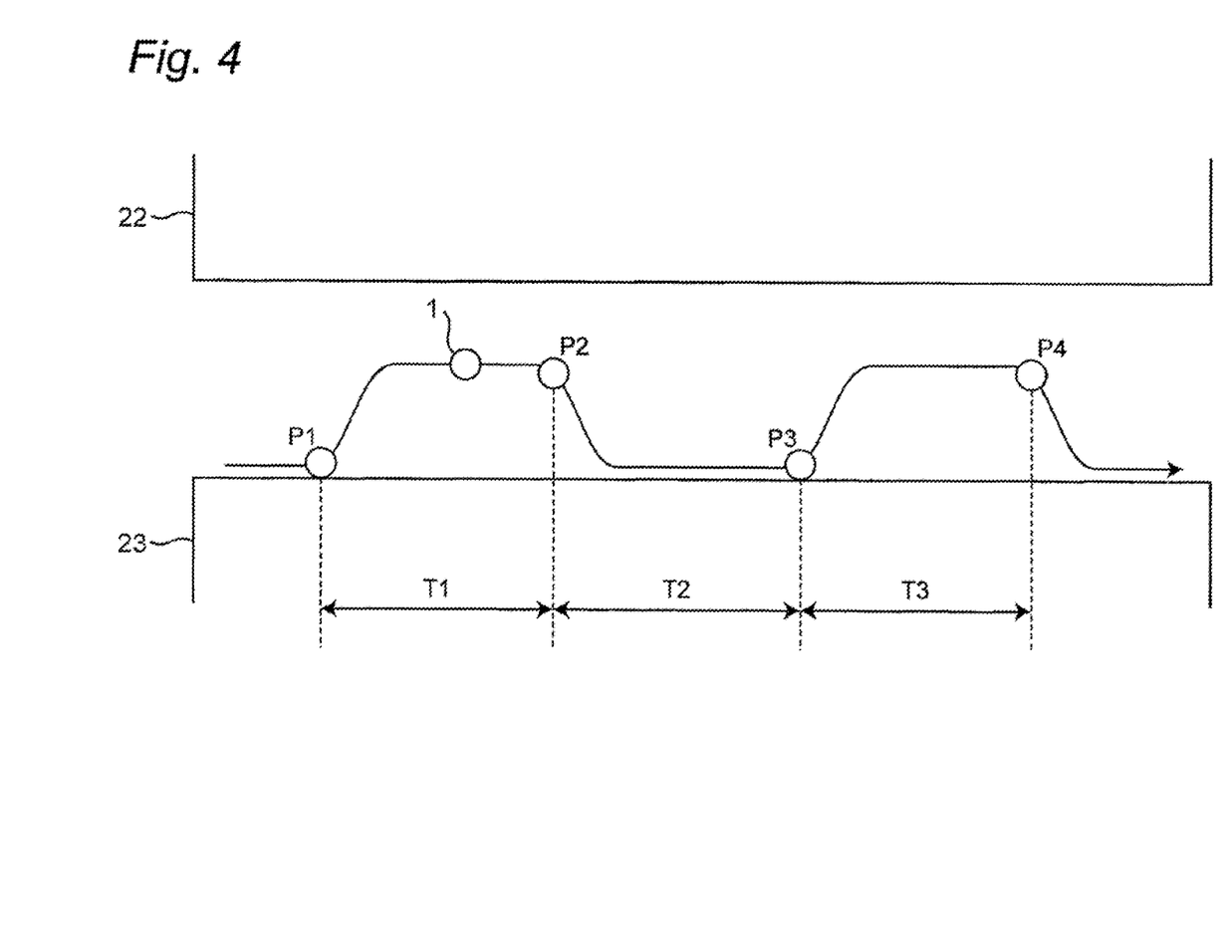
FIG. 4 is a diagram showing an example of a movement trajectory of frequency-modulated dielectric particles in the analysis device.

Hereinafter, a crossover frequency analyzing process in the analyzer 20 will be described. FIG. 4 is a diagram showing an example of a movement trajectory of the cancer cell 1 between the pair of electrodes 22, 23. In the following, the crossover frequency analyzing process for the cancer cell 1 will be described. The crossover frequency analyzing process for a cell other than the cancer cells 1, such as the white blood cell, is similar to the following process. In FIG. 4, the trajectories P1, P2, P3, P4 are positions of the cancer call 1 at times t1, t2, t3, t4 in FIG. 3. As shown in FIGS. 3 and 4, when the frequency of the AC voltage applied between the electrodes 22, 23 is lower than the crossover frequency COF, a negative dielectrophoretic force (repulsive force) acts on the cancer cell 1 and the electrodes 22, 23 repel the cell 1, and the cell 1 flows in the flow channel 5 while moving apart from the electrodes 22, 23 (e.g., sections T1, T3). On the other hand, when the frequency of the AC voltage applied between the electrodes 22, 23 is higher than the crossover frequency COF, a positive dielectrophoretic force (attractive force) acts on the cancer cell 1, and the cancer cell 1 flows in the flow channel 5 while being attracted to the electrodes 22, 23 (e.g., section T2).

Based on the movement trajectory which changes as shown in FIG. 4, for example, the controller 26 obtains the positions P2, P4 of the cancer cell 1 at which the dielectrophoretic force switches from the repulsive force to the attractive force. Then, from the positions P2, P4, the controller 26 obtains timing t2, t4, at which the dielectrophoretic force switches from the repulsive force to the attractive force. The controller 26 obtains the frequency of the AC voltage of the power supply 24 at the timing t2, t4 as the crossover frequency from the control information to the power supply 24 at the timing t2, t4. As thus described, the crossover frequency (COF) of the cancer cell 1 can be determined.

3. Summary

As described above, the replacement unit 10 and the analyzer 20 constitute the analysis device 200. The analysis device 200 according to the present embodiment is an analysis device for analyzing a crossover frequency at which a dielectrophoretic force on the cells such as the circulating cancer cells (dielectric particles) 1 and the white blood cells switches from the repulsive force to the attractive force or from the attractive force to the repulsive force, the analysis device including the flow channel (first flow channel) 5, the pair of electrodes (first electrodes) 22, 23, the power supply (first power supply) 24, the imaging unit 25, and the controller (analyzer) 26. A sample solution containing the cells such as the cancer cells 1 and the white blood cells in the dielectrophoretic liquid flows through the flow channel 5. The pair of electrodes 22, 23 is arranged in the flow channel 5, and the power supply 24 applies a frequency-modulated AC voltage to the pair of electrodes 22, 23. The imaging unit 25 captures an image of a movement trajectory of each of the cells such as the cancer cells 1 and the white blood cells flowing between the pair of electrodes 22, 23 in the flow channel 5. The controller 26 obtains the crossover frequency of the cells such as the cancer cells 1 and the white blood cells based on the captured images of the movement trajectory.

Further, the separation device 100 according to the present embodiment is a separation device for separating the cells such as the cancer cells 1 and the white blood cells, the separation device including the above analysis device 200, the pair of electrodes (second electrodes) 32, 33, the power supply (second power supply) 34, and the controller 26. The pair of electrodes 32, 33 is arranged at a stage subsequent to the pair of electrodes 22, 23 in the flow channel 5 of the analysis device 200, and the power supply 34 applies an AC voltage of a predetermined frequency to the pair of electrodes 32, 33. The controller 26 controls the predetermined frequency based on the crossover frequency obtained by the analysis device 200 with respect to the dielectric particles so that the cancer cells 1 are subjected to dielelectrophoresis is at the time of passage of the cells such as the cancer cells 1 and the white blood cells analyzed by the analysis device 200 through the pair of electrodes 32, 33 in the flow channel 5.

According to the present embodiment, the analysis is performed on the crossover frequency of the cells such as the cancer cells 1 and the white blood cells in the flow channel 5, into which the sample solution containing the cells such as the cancer cells 1 and the white blood cells is introduced. Therefore, it is possible to easily analyze the crossover frequency of the cells such as the cancer cells 1 and the white blood cells without performing operation to place dielectric particles between fine microelectrodes as in the conventional case, and it is possible to use the cancer cells 1 used for the analysis and separation after the analysis and separation (non-destructive analysis).

Further, the analysis device 200 according to the present embodiment further includes the replacement unit 10 that includes the flow channel (second flow channel) 11 which is disposed at a stage prior to the flow channel 5 and into which a suspension containing the cells such as the cancer cells 1 and the white blood cells and the dielectrophoretic liquid (DEP liquid) are introduced, and the branched flow channels 12 that branch from the flow channel 11. The replacement unit branches a solution in the suspension into the branched flow channels 12 to replace the solution in the suspension with the DEP liquid and produce the sample solution. The replacement unit 10 individually and sequentially leads the cells of the desired size or larger such as the cancer cells 1 and the white blood cells in the sample solution from the flow channel 11 to the flow channel 5.

Thus, by introducing the suspension containing the cells such as the cancer cells 1 and the white blood cells and the DEP liquid into the flow channel 11 provided with the branched flow channels 12, the solution in the suspension is replaced with the DEP liquid to generate a sample solution containing the cells such as the cancer cells 1 and the white blood cells in the DEP liquid. It is thus possible to adjust the conductivity of the sample solution by adjusting the conductivity of the DEP liquid alone.

Therefore, as compared with the conventional solution replacement (buffer replacement) in which the conductivity of the sample solution is adjusted by mixing the suspension and the DEP liquid and adjusting the concentration of the sample solution, it is possible to reduce the time for adjusting the conductivity of the sample solution, and to reduce time-dependent fluctuations in the crossover frequency of the cells such as the cancer cells 1 and the white blood cells by solution replacement.

In addition, as compared with the conventional solution replacement described above, it is possible to adjust the conductivity of the sample solution in an easy and highly accurate manner, and to reduce the analysis variation of the crossover frequency due to the conductivity variation of the sample solution.

Other Embodiments

In the above embodiment, bacteria and cells are exemplified as the test targets of the present system. The test target in the present system is not limited to bacteria and cells but may be other dielectric particles such as microorganisms, fungi, spores, and viruses.

In the above embodiment, the controller 26 that analyzes the crossover frequency at the timing when the dielectrophoretic force switches from the repulsive force to the attractive force (e.g., t2, t4 in FIG. 3) is described, but the controller 26 may analyze the crossover frequency at the timing when the dielectrophoretic force switches from the attractive force to the repulsive force (e.g., t1, t3 in FIG. 3).

In the above embodiment, the separator 30 is described as applying to the electrodes 32, 33 an AC voltage with a frequency higher than the crossover frequency analyzed by the analyzer 20 and causes a positive dielectrophoretic force (attractive force) to act on the cancer cells 1 passing through the electrodes 32, 33, thus separating the cancer cells 1. However, the separator 30 is not limited thereto. The separator 30 may apply to the electrodes 32, 33 an AC voltage with a frequency lower than the crossover frequency analyzed by the analyzer 20 and may cause a negative dielectrophoretic force (repulsive force) to act on the cancer cells 1 passing through the electrodes 32, 33, thus separating the cancer cells 1. In this case, in FIG. 2, the electrodes 32, 33 repel the cancer cell 1, and the cancer cell 1 flows in the flow channel 5 along the extending direction of the electrodes 32, 33, while moving apart from the electrodes 32, 33, to be collected into the collection unit 6.

The separator 30 may apply to the electrodes 32, 33 an AC voltage with a frequency equal to the crossover frequency analyzed by the analyzer 20 so as not to cause a dielectrophoretic force to act on the cancer cells 1 passing through the electrodes 32, 33. In this case, in FIG. 2, the cancer cell 1 flows in the flow channel 5 without dielectrophoresis and reaches between the collection unit 6 and the collection unit 7. In this case, a collection unit may be provided between the collection unit 6 and the collection unit 7.

In the above embodiment, the separator 30 is described as applying to the electrodes 32, 33 an AC voltage having a frequency that is higher than the crossover frequency analyzed by the analyzer 20 with respect to the cancer cells 1 and is in the vicinity of the crossover frequency analyzed by the analyzer 20 with respect to the cells other than the cancer cells 1, such as the white blood cells, and causes a positive dielectrophoretic force (attractive force) to act on the cancer cells 1 passing through the electrodes 32, 33, thus separating the cancer cells 1. On the other hand, the separator 30 may apply to the electrodes 32, 33 an AC voltage having a frequency that is lower than the crossover frequency analyzed by the analyzer 20 with respect to the cells other than the cancer cells 1, such as the white blood cells and is in the vicinity of the crossover frequency analyzed by the analyzer 20 with respect to the cancel cells 1, and cause a negative dielectrophoretic force (repulsive force) to act on the cells other than the cancer cells 1, such as the white blood cells passing through the electrodes 32, 33, thus separating the cancer cells 1 from the cells other than the cancer cells 1. At this time, the negative dielectrophoretic force (repulsive force) acts on the cells other than the cancer cells 1, such as the white blood cells, and the electrodes 32, 33 repel the cells such as the white blood cells, and the cells flow in the flow channel 5 along the extending direction of the electrodes 32, 33, while moving apart from the electrodes 32, 33, and are collected into the collection unit 6. On the other hand, the dielectrophoretic force does not act on the cancer cells 1, or even if the positive or negative dielectrophoretic force (attractive force or repulsive force) acts, the dielectrophoretic force is relatively small. Therefore, the cancer cells 1 are allowed to flow by the flow in the flow channel 5 and collected into the collection unit 7.

The invention claimed is:

1. An analysis device for analyzing a crossover frequency at which a dielectrophoretic force on dielectric particles switches from a repulsive force to an attractive force or from the attractive force to the repulsive force, the analysis device comprising:
   a first flow channel through which a sample solution containing the dielectric particles in dielectrophoretic liquid flows,
   a pair of first electrodes arranged in the first flow channel,
   a first power supply that applies a frequency-modulated AC voltage to the pair of first electrodes,
   an imaging unit that captures an image of a movement trajectory of each of the dielectric particles flowing between the pair of first electrodes in the first flow channel; and
   a controller that analyzes a change in the movement trajectory along which the dielectric particles flow in the first flow channel and determines the crossover frequency of the dielectric particles based on the change in the movement trajectory in the captured image.

2. The analysis device according to claim 1, further comprising a replacement unit that includes:
   a second flow channel which is disposed at a stage prior to the first flow channel and into which a suspension containing the dielectric particles and the dielectrophoretic liquid are introduced, and
   a branched flow channel that branches from the second flow channel,
   wherein the replacement unit is configured for branching a solution in the suspension into the branched flow channel to replace the solution in the suspension with the dielectrophoretic liquid and produce the sample solution, and
   wherein the replacement unit individually and sequentially leads the dielectric particles in the sample solution from the second flow channel to the first flow channel.

3. A separation device for separating dielectric particles, comprising:
   the analysis device according to claim 1;
   a pair of second electrodes arranged at a stage subsequent to the pair of first electrodes in the first flow channel of the analysis device;
   a second power supply that applies an AC voltage of a predetermined frequency to the pair of second electrodes; and
   a controller that controls the predetermined frequency based on the crossover frequency obtained by the analysis device with respect to the dielectric particles so that the dielectric particles analyzed by the analysis device are subjected to dielectrophoresis while the dielectric particles pass through the pair of second electrodes in the first flow channel.

4. The separation device according to claim 3, wherein the analysis device further comprises a replacement unit that includes:
   a second flow channel which is disposed at a stage prior to the first flow channel and into which a suspension containing the dielectric particles and the dielectrophoretic liquid are introduced, and
   a branched flow channel that branches from the second flow channel,
   wherein the replacement unit is configured for branching a solution in the suspension into the branched flow channel to replace the solution in the suspension with the dielectrophoretic liquid and produce the sample solution, and
   wherein the replacement unit individually and sequentially leads the dielectric particles in the sample solution from the second flow channel to the first flow channel.

* * * * *